(12) United States Patent
Deshpande et al.

(10) Patent No.: US 8,686,051 B2
(45) Date of Patent: Apr. 1, 2014

(54) PHARMACEUTICAL COMPOSITION FOR TREATMENT OF DIABETIC COMPLICATIONS

(75) Inventors: Supreet K. Deshpande, Pune (IN); Sudhir A. Kulkarni, Pune (IN); Reena R. Gollapudy, Pune (IN)

(73) Assignee: VLife Sciences Technologies Pvt. Ltd., Pune (IN)

( * ) Notice: Subject to any disclaimer, the term of this patent is extended or adjusted under 35 U.S.C. 154(b) by 207 days.

(21) Appl. No.: 12/524,823

(22) PCT Filed: Jan. 24, 2008

(86) PCT No.: PCT/IN2008/000044
§ 371 (c)(1), (2), (4) Date: Jul. 28, 2009

(87) PCT Pub. No.: WO2008/093356
PCT Pub. Date: Aug. 7, 2008

(65) Prior Publication Data
US 2011/0021526 A1 Jan. 27, 2011

(30) Foreign Application Priority Data
Jan. 29, 2007 (IN) .......... 1960/MUM/2006

(51) Int. Cl.
*A61K 31/045* (2006.01)
*A61K 31/07* (2006.01)

(52) U.S. Cl.
USPC .......... 514/724; 514/725

(58) Field of Classification Search
USPC .......... 514/724, 725
See application file for complete search history.

(56) References Cited

U.S. PATENT DOCUMENTS

| | | | |
|---|---|---|---|
| 3,337,628 A * | 8/1967 | Crowther et al. | 564/349 |
| 3,655,663 A * | 4/1972 | Wasson | 544/134 |
| 4,593,119 A * | 6/1986 | Erhardt et al. | 560/42 |
| 5,362,757 A | 11/1994 | Young et al. | |
| 2003/0144206 A1 | 7/2003 | Knudsen et al. | |

FOREIGN PATENT DOCUMENTS

| | | | |
|---|---|---|---|
| EP | 1 790 353 A1 | | 5/2007 |
| JP | 58-206519 | | 12/1983 |
| JP | 58206519 A | * | 12/1983 |
| JP | 2005-516968 A | | 6/2005 |
| WO | WO 00/35439 A1 | | 6/2000 |
| WO | WO 03/059372 A2 | | 7/2003 |
| WO | WO 2006/108176 A2 | | 10/2006 |

OTHER PUBLICATIONS

McCrea et al., "Transdermal timolol: beta blockade and plasma concentrations after application for 48 hours and 7 days", Pharmacotherapy, vol. 10, No. 4, pp. 289-293 (1990).*
Abstract of English Translation of JP 58206519 A (1983).*
Decision of Apr. 8, 2004 (EP 0 536 607) (Forty-four (44) pages).
European Search Report dated Jul. 27, 2010 (Four (4) pages).
Holman Rury et al., "Efficacy of atenolol and captopril in reducing risk of macrovascular and microvascular complications in type 2 diabetes: UKPDS 39", BMJ, BMJ Publishing Group, vol. 317, No. 7160, Sep. 12, 1998, pp. 713-720, XP009100574.
Cotter M. A. et al., "Neuroprotective effects of carvedilol in diabetic rats: prevention of defective peripheral nerve perfusion and conduction velocity", Naunyn-Schmiedeberg's Archives of Pharmacology, Springer, Berlin, Germany, vol. 351, No. 6, Jan. 1, 1995, pp. 630-635, XP009101086.
Ono R. et al., "Effects of topical nipradilol on retinal microcirculation of early diabetic retinopathy", Investigative Ophthalmology, Hagerstown, Maryland, vol. 45, No. suppl. 2, Apr. 1, 2004, pp. 3201-B836, XP009101076.
International Search Report dated Jun. 17, 2008 (three (3) pages).
Tim Fulmer, "β-blocking Wounds", Targets & Mechanisms, 2(7): pp. 1-3, SciBX 2009.
Sivamani et al., "Stress-Mediated Increases in Systemic and Local Epinephrine Impair Skin Wound Healing: Potential New Indication for Beta Blockers", PLos Med. 6(1);e1000012: pp. 105-115, 2009.
Pullar et al., "β2-Adrenergic receptor activation delays wound healing", FASEB J. 20: pp. 76-86, 2006.
Chen et al., "β-Adrenergic Receptor Activation Inhibits Keratinocyte Migration via a Cyclic Adenosine Monophosphate-independent Mechanism", J Invest Dermatol, 119: pp. 1261-1268, 2002.
Romana-Souza et al., "Propranolol improves cutaneous wound healing in streptozotocin-induced diabetic rats", European Journal of Pharmacology 611: pp. 77-84, 2009.
Oyama et al., "The role of polyol pathway in high glucose-induced endothelial cell damages", Diabetes Research and Clinical Practice 73: pp. 227-234, 2006.
H. Brem & M. Tomic-Canic, "Cellular and molecular basis of wound healing in diabetes", J. Clin. Invest. 117: pp. 1219-1222, 2007.
UK Prospective Diabetes Study Group, Efficacy of atenolol and captopril in reducing risk of macrovascular and microvascular complications in type 2 diabetes: UKPDS 39, BMJ 317: pp. 713-720, 1998.
Ono et al., "Effects of topical nipradilol on retinal microcirculation of early diabetic retinopathy", Invest. Ophthalmol. Vision Sci., E-abstract 3201, 2004.

(Continued)

*Primary Examiner* — Kevin E Weddington
(74) *Attorney, Agent, or Firm* — Crowell & Moring LLP

(57) ABSTRACT

A method for treating diabetic complications by administration of a beta-blocker is disclosed. Diabetic complications arise from diabetes and have few or no existing treatment options. The present invention describes the use of a beta-blocker in the treatment of a diabetic. The present invention also describes the inhibition of aldose reductase, one of the chief causative factors of diabetic complications. Also provided are methods of diabetic wound healing. Compositions for treating diabetic complications, such as diabetic wounds, are disclosed. The present invention includes employing a topical formulation of a beta-blocker, having substantially no antibacterial activity, to improve the process of diabetic wound healing. The present invention also involves increasing the rate of collagen accumulation of the healing epithelialized tissue in the wound of a diabetic individual.

10 Claims, No Drawings

(56) References Cited

OTHER PUBLICATIONS

M. A. Cotter & N. E. Cameron, "Neuroprotective effects of carvedilol in diabetic rats; prevention of defective peripheral nerve perfusion and conduction velocity", Naunyn Schmiedeberg's Arch. Pharmacol 351: pp. 630-635, 1995.

Romana-Souza et al., β-1 and β-2, but not α-1 and α-2, adrenoceptor blockade delays rat cutaneous wound healing (Abstract only), Wound Repair Regen. 17: pp. 230-239, 2009.

Pullar et al., "β-Adrenergic Receptor Antagonists Accelerate Skin Wound Healing", J. Biol. Chem. 281/30: pp. 21225-21235, 2006.

http://www.merriam-webster.com/dictionary/transdermal (copyright 2012, accessed: Jul. 5, 2012).

http://www.merriam-webster.com/dictionary/topical (copyright 2012, accessed: Jul. 5, 2012).

http://www.medicinenet.com/script/main/art.asp?articlekey=45817 (last editorial review: Sep. 22, 2010, copyright 2012, accessed: Jul. 5, 2012).

Sintetos et al. "Pharmacokinetics and pharmacodynamics of esmolol administered as an intravenous bolus," vol. 41, No. 1, Clin Pharmacol Ther, Jan. 1987, pp. 112-117.

Volz-Zang, et al. "Esmolol, an ultrashort-acting, selective $β_1$-adrenoceptor antagonist: pharmacodynamic and pharmacokinetic properties," Eur J of Clin Pharmacol, 1994, 46: 399-404.

Abstract of Jahn et al., "Beta 1-adrenoceptor subtype selective antagonism of esmolol and its major metabolite in vitro and in man. Investigations using tricresylphosphate as red blood cell carboxylesterase inhibitor," Arzneimittelforschung. May 1995; 45(5): 536-41. (one (1) page).

Brevibloc label (2007) (twenty-one (21) pages).

John J. Reynolds, "The Molecular and Cellular Interactions Involved in Connective Tissue Destruction", British Journal of Dermatology, Jun. 1985, pp. 715-723, vol. 112, No. 6. (Ten (10) sheets).

John A. Galloway et al., "Diabetes and Surgery", The American Journal of Medicine, Feb. 1963, pp. 177-191, vol. 34. (Seventeen (17) sheets).

Stephen H. Pearl et al., "Diabetes and Healing: A Review of the Literature", The Journal of Foot Surgery, May/Jun. 1988, pp. 268-270. vol. 27, No. 3. (Four (4) sheets).

John D. Bagdade et al., "Impaired Granulocyte Adherence—A Reversible Defect in Host Defense in Patients with Poorly Controlled Diabetes", The Journal of the American Diabetes Association, Jun. 1978, pp. 677-681, vol. 27, No. 6. (Six (6) sheets).

Charles M. Nolan et al., "Further Characterization of the Impaired Bactericidal Function of Granulocytes in Patients with Poorly Controlled Diabetes", The Journal of the American Diabetes Association, Sep. 1978, pp. 889-894, vol. 27, No. 9. (Seven (7) sheets).

Alastair G. Mowat et al., "Chemotaxis of Polymorphonuclear Leukocytes from Patients with Rheumatoid Arthritis", The Journal of Clinical Investigation, 1971, pp. 2541-2549, vol. 50. (Nine (9) sheets).

David G. Greenhalgh et al., "PDGF and Fgf Stimulate Wound Healing in the Genetically Diabetic Mouse", American Journal of Pathology, Jun. 1990, pp. 1235-1246, vol. 136, No. 6. (Twelve (12) sheets).

Gary D. Salomon et al., "The Local Effects of Cachectin/Tumor Necrosis Factor on Wound Healing", Annals of Surgery, Jul. 1991, pp. 175-180, vol. 214, No. 1. (Seven (7) sheets).

David Schwartz, "The Proliferation of Elastic Fibres After Skin Incisions in Albino Mice and Rats: a Light and Elctron Microscopic Study", Journal of Anatomy, Nov. 1977, pp. 401-411, vol. 124, Part 2. (Twelve (12) sheets).

William H. Goodson et al., "Wound Collagen Accumulation in Obese Hyperglycemic Mice", The Journal of the American Association, Apr. 1986, pp. 491-495, vol. 35, No. 4. (Six (6) sheets).

Noriyuki Sakata et al., "Effects of Advanced Glycation End-products on the Proliferation and Fibronectin Production of Smooth Muscle Cells", Journal of Atherosclerosis and Thrombosis, 2000, pp. 169-176, vol. 7, No. 3. (Eight (8) sheets).

D. Kirk Ways et al., "The Role of Protein Kinase C in the Development of the Complications of Diabetes", Vitamins and Hormones, 2001, pp. 149-193, vol. 60. (Forty-seven (47) sheets).

Ryuichi Mashima et al., "Oxidants and antioxidants in atherosclerosis", Current Opinion in Lipidology, Aug. 2001, pp. 411-418, vol. 12, No. 4. (Nine (9) sheets).

N. Sakamoto et al., "Polyol pathway and its role in diabetic complications", Elsevier Science Publishers B.V., Amsterdam, 1988. (Nine (9) sheets).

James J. Reidy et al., "Effect of topical β blockers on corneal epithelial wound healing in the rabbit", British Journal of Ophthalmology, May 1994, pp. 377-380, vol. 78, No. 5. (Five (5) sheets).

Mitsuhiro Denda et al., "β2-Adrenergic Receptor Antagonist Accelerates Skin Barrier Recovery and Reduces Epidermal Hyperplasia Induced by Barrier Disuption", The Journal of Investigative Dermatology, 2003, pp. 142-148, vol. 121, No. 1. (Seven (7) sheets).

R. C. Lindenschmidt et al., "Propranolol-Induced Elevation of Pulmonary Collagen", The Journal of Pharmacology and Experimental Therapeutics, Feb. 1985, pp. 346-350 vol. 232, No. 2. (Six (6) sheets).

Hans-Dietmar Beer et al., "Reduced Expression of PDGF and PDGF Receptors During Impaired Wound Healing", The Journal of Investigative Dermatology, Aug. 1997, pp. 132-138, vol. 109, No. 2. (Seven (7) sheets).

David L. Steed et al., "Clinical evaluation of recombinant human platelet-derived growth factor for the treatment of lower extremity diabetic ulcers", Journal of Vascular Surgery, Jan. 1995, pp. 71-81, vol. 21, No. 1. (Eleven (11) sheets).

Daniela Bruch-Gerharz et al., "Nitric Oxide in Human Skin: Current Status and Future Prospects", The Journal of Investigative Dermatology, Jan. 1998, pp. 1-7, vol. 110, No. 1. (Seven (7) sheets).

Michael R. Schaeffer, MD et al., "Diabetes-impaired healing and reduced wound nitric oxide synthesis: A possible pathophysiologic correlation", Surgery, May 1997, pp. 513-519, vol. 121, No. 5. (Eight (8) sheets).

Aristidis Veves et al., "Endothelial Dysfunction and the Expression of Endothelial Nitric Oxide Synthetase in Diabetic Neuropathy, Vascular Disease, and Foot Ulceration", Diabetes, Mar. 1998, pp. 457-463, vol. 47. (Seven (7) sheets).

Marianna Huszka et al., "The Association of Reduced Endothelium Derived Relaxing Factor-No Production with Endothelial Damage and Increased in Vivo Platelet Activation in Patients with Diabetes Mellitus", Thrombosis Research, 1997, pp. 173-180, vol. 86, No. 2. (Nine (9) sheets).

Stephen B. Williams et al., "Impaired Nitric Oxide-Mediated Vasodilation in Patients With Non-Insulin-Dependent Diabetes Mellitus", Journal of the American College of Cardiology, Mar. 1, 1996, pp. 567-574, vol. 27, No. 3. (Nine (9) sheets).

Joseph S. Beckman, "The Physiological and Pathological Chemistry of Nitric Oxide", Nitric Oxide: Principles and Actions, 1996, Chapter 1, pp. 1-82. (Eighty-four (84) sheets).

Salvador Moncada et al., "The L-Arginine-Nitric Oxide Pathway", The New England Journal of Medicine, Dec. 30, 1993, pp. 2002-2012, vol. 329, No. 27. (Twelve (12) sheets).

Michael R. Schaeffer et al., "Nitric Oxide Metabolism in Wounds", Journal of Surgical Research, Jul. 15, 1997, pp. 25-31, vol. 71, No. 1. (Eight (8) sheets).

Andreas Papapetropoulos et al., "Nitric Oxide Production Contributes to the Angiogenic Properties of Vascular Endothelial Growth Factor in Human Endothelial Cells", The Journal of Clinical Investigation, Dec. 15, 1997, pp. 3131-3139, vol. 100, No. 12. (Ten (10) sheets).

Eisei Noiri et al., "Nitric oxide is necessary for a switch from stationary to locomoting phenotype in epithelial cells", American Journal of Physiology, Mar. 1996, pp. C794-C802, vol. 270, No. 3. (Ten (10) sheets).

Michael R. Schaeffer et al., "Nitric Oxide Regulates Wound Healing", Journal of Surgical Research, Jun. 1996, pp. 237-240, vol. 63, No. 1. (Five (5) sheets).

Allan M. Lefer et al., "The role nitric oxide and cell adhesion molecules on the microcirculation in ischaemia-reperfusion", Cardiovascular Research, Oct. 1996, pp. 743-751, vol. 32, No. 4. (Ten (10) sheets).

Ying H. Shen et al., "Nitric oxide induces and inhibits apoptosis through different pathways", FEBS Letters, Aug. 14, 1998, pp. 125-131, vol. 433, No. 1,2. (Eight (8) sheets).

(56) References Cited

OTHER PUBLICATIONS

Soon Chan Um et al., "Involvement of Nitric Oxide in Survival of Random Pattern Skin Flap", Plastic and Reconstructive Surgery, Mar. 1998, pp. 785-792, vol. 101, No. 3. (Nine (9) sheets).

Glenn F. Pierce et al., "Transforming growth factor β reverses the glucocorticoid-induced wound-healing deficit in rats: Possible regulation in macrophages by platelet-derived growth factor", Proceedings of the National Academy of Sciences USA, Apr. 1989, pp. 2229-2233, vol. 86. (Five (5) sheets).

P. M. Rhodes et al., "The L-Arginine: Nitric Oxide Pathway is the Major Source of Plasma Nitrite in Fasted Humans", Biochemical and Biophysical Research Communications, Apr. 17, 1995, pp. 590-596, vol. 209, No. 2. (Eight (8) sheets).

L. Castillo et al., "Splanchnic metabolism of dietary arginine in relation to nitric oxide synthesis in normal adult man", Proceedings of the National Academy of Sciences USA, Jan. 1993, pp. 193-197, vol. 90. (Five (5) sheets).

Chris Baylis et al., "Measurement of nitrate and nitrate levels in plasma and urine—what does this measure tell us about the activity of the endogenous nitric oxide system?", Current Opinion in Nephrology and Hypertension, Jan. 1998, pp. 59-62, vol. 7, No. 1. (Five (5) sheets).

P. Suryanarayana et al., "Inhibition of aldose reductase by tannoid principles of Emblica officinalis : Implications for the prevention of sugar cataract", Molecular Vision, Mar. 12, 2004, pp. 148-154, vol. 10. (Seven (7) sheets).

J. Mark Petrash et al., "Involvement of Cysteine Residues in Catalysis and Inhibition of Human Aldose Reductase", The Journal of Biological Chemistry, Dec. 5, 1992, pp. 24833-24840, vol. 267, No. 34. (Eight (8) sheets).

Selma Hayman et al., "Isolation and Properties of Lens Aldose Reductase", The Journal of Biological Chemistry, Feb. 1965, pp. 877-882, vol. 240, No. 2. (Six (6) sheets).

John I. Malone et al., "Red Cell Sorbitol: An Indicator of Diabetic Control", The Journal of the American Diabetes Association, Nov. 1980, pp. 861-864, vol. 29, No. 11. (Five (5) sheets).

\* cited by examiner

PHARMACEUTICAL COMPOSITION FOR TREATMENT OF DIABETIC COMPLICATIONS

FIELD OF INVENTION

A method for treating diabetic complications by administration of a beta-blocker is disclosed. Diabetic complications arise from diabetes and have few or no existing treatment options. The present invention describes the use of beta-blockers in the treatment of diabetic complications. The present invention also describes the inhibition of aldose reductase, one of the chief causative factors of diabetic complications. Also provided are methods of diabetic wound healing. Compositions for treating diabetic complications, such as diabetic wounds, are disclosed. The present invention includes employing a topical formulation of a beta-blocker, having substantially no antibacterial activity, to improve the process of diabetic wound healing. The present invention also involves increasing the rate of collagen accumulation of the healing epithelialized tissue in the wound of a diabetic individual.

BACKGROUND OF INVENTION

The worldwide incidence of diabetes has increased from an estimated 30,000,000 patients in 1985 to an estimated 245,000,000 patients in 2007, and will further increase to 380,000,000 by 2025 (Source: International Diabetes Federation). The treatment cost of diabetes and diabetic complications is reaching $232,000,000,000 in 2007 and may be expected to be over $302,500,000,000 by 2025. Chronic diabetes gives rise to several diabetic complications such as diabetic neuropathy, diabetic nephropathy, diabetic cardiomyopathy, diabetic retinopathy, diabetic cataract, diabetic cystopathy, diabetic corneal keratopathy, diabetic dermopathy, diabetic microangiopathy, myocardial infarction, macular edema, impaired neural conduction and diabetic wounds.

Treatment of diabetic complications is independent of blood glucose level control. Thus, standard anti-diabetic drugs are not suitable as treatment options for diabetic complications. There is an immediate requirement for new compositions and treatments for diabetic complications.

One of the major underlying problem facing diabetics is impaired wound healing. Fifteen percent of all people with diabetes (2.6 million) are expected to develop foot ulcers during their lifetime. These ulcers tend to be chronic in nature, as they do not heal or heal extremely slowly. Currently, there are approximately 750,000 patients with diabetic foot ulcers in the United States, 980,000 in Europe and 1.1 million in the rest of the world, totaling 2.8 million patients. Diabetic foot ulcers are a serious problem, as up to 25% of diabetic foot ulcers will eventually require amputation. The medical importance of diabetic wound healing cannot be overstated. The capacity to heal is central to human well being, as wound healing enables a patient to overcome traumatic injury, surgery, and wounds due to metabolic disorders such as diabetes, microbial or other physical or chemical agents.

The ineffective healing of wounds is a serious problem in diabetes, contributing to increased morbidity (J. J. Reynolds, British J Dermatol, 112 715-723 (1985); J. A. Galloway and C. R. Shuman, Am J Med, 34 177-191 (1963); and S. H. Pearl and I. O. Kanat, J Foot Surg, 27, 268-270 (1988)). The reparative response in wound healing is orchestrated by multiple cellular elements which work together in many ways, including infiltration of the lesion by inflammatory effector cells. Subsequent to this, fibroblastic elements together with inflammatory effector cells provide antibacterial mechanisms and promote removal of necrotic tissue, as well as the laying down of new connective tissue. A fundamental disorder of glucose metabolism may disturb these complex and interactive protective processes.

Previous work has suggested that cellular dysfunction in diabetic wound healing involves defective neutrophil function (J. D. Bagdade et al., Diabetes, 27, 677-681 (1978); C. M. Nolan et al., Diabetes, 27, 889-894 (1978); A. G. Mowat and J. Baum, J. Clin Invest December, 50, 2541-2549 (1971)), delayed infiltration of the wound with inflammatory cells (D. G. Greenhalgh et al., Am J Pathol, 136, 1235 (1990) and Fahey et al., Surg 214, 175-180 (1991)), decreased production of collagen (W. H. Goodson and T. K. Hunt, J Anal, 124, 401-411 (1977) and W. H. Goodson and T. K. Hunt, Diabetes April, 35, 491-495 (1986)), and diminished activity of endogenous growth factors, such as basic fibroblast growth factor, which could provide a basis for the slower formation of granulation tissue and wound closure.

Over 100 known physiologic factors contribute to wound healing deficiencies in individuals with diabetes (Oyama, et al. Diabetes: Research and Clinical Practice 73, 227-234 (2006); H. Brem and M. Tomic-Canic, J. Clin. Invest., 117, 1219-1222 (2007)). These factors include decreased or impaired growth factor production, angiogenic response, macrophage function, collagen accumulation, epidermal barrier function, quantity of granulation tissue, keratinocyte and fibroblast migration and proliferation, number of epidermal nerves, bone healing, and balance between the accumulation of extracellular matrix (ECM) components and their remodeling by metalloproteinases (MMPs). Wound healing occurs as a cellular response to injury and involves activation of keratinocytes, fibroblasts, endothelial cells, macrophages, and platelets. Many growth factors and cytokines released by these cell types are needed to coordinate and maintain healing. Molecular analyses of biopsies from the epidermis of patients have identified pathogenic markers that correlate with delayed wound healing. These include the over expression of c-myc and nuclear localization of β-catenin. Coupled with a reduction in and abnormal localization of epidermal growth factor receptor (EGFR) and activation of the glucocorticoid pathway, keratinocyte migration is inhibited. At the non healing edge (callus) of diabetic foot ulcers (DFUs), keratinocytes show an absence of migration, hyper proliferation, and incomplete differentiation. Fibroblasts demonstrate a phenotypic change as well as decreased migration and proliferation.

The diabetic foot ulcer etiology is complex, and wound healing is often not very successful for a variety of reasons. The diabetic foot ulcer's etiology is associated with peripheral vascular disease, autonomic neuropathy and endothelial dysfunction. Metabolic conditions that are not optimal for wound-healing delay the process even more (hyperglycemia, hyperlipidemia, hyperinsulinemia, pro-coagulative state) and may also be present. Wound healing is a complex process characterized by three overlapping phases: inflammation, tissue formation and tissue remodeling (H. Brem and M. Tomic-Canic, J. Clin. Invest., 117, 1219-1222 (2007)). This sequential process emanates by the interaction of cells in the dermis and epidermis, in parallel with the release of chemical mediators from inflammatory cells, fibroblasts and keratinocytes. During tissue formation, growth factors synthesized by local and migratory cells stimulate fibroblasts to migrate into the wound where they proliferate and construct an extracellular matrix. Diabetes is known to be associated with a variety of alterations in connective tissue metabolism, as a result of which diabetics face the problem of poor wound healing. The common features observed during diabetic wound healing in rats are inflammation, slow beginning of the initial healing phase which tends to prolong healing time, lower density of neutrophils in healing areas and failure in the replacement of neutrophils by macrophages in the areas where healing occurs. Cutaneous wound healing is a complex and well orchestrated biological process requiring the coordinated migration and proliferation of both keratinocytes and fibroblasts, as well as other cell types. Wounding the epidermis generates cytokines, growth factors, proteases and initiates the synthesis of extracellular matrix components, all of which can regulate the processes of keratinocyte migration and proliferation essential for re-epithelialization.

Loss of collagen related to diabetes may be due to decreased levels of synthesis or enhanced metabolism of newly synthesized collagen or both. These qualitative and quantitative abnormalities contribute to the impaired wound healing observed in diabetic condition.

Various mechanisms of cell injuries in diabetes mellitus have been reported (Sakata et al., J. Atheroscler. Thromb. 3, 169-176 (2000); D. K. Ways, M. J. Sheetz, Vitam. Horm. 60, 149-193 (2000); Mashima, et al., Curr. Opin. Lipidol. 4, 411-418 (2001)), including accelerated glycation, increased protein kinase C activity and increased oxidative stress, but the precise mechanism is not fully understood. Hotta's group (N. Sakamoto, J. H. Kinoshita, P. F. Kador, N. Hotta, Polyol Pathway and its Role in Diabetic Complications, Elsevier Science B.V., Amsterdam, 1988) proposed the involvement of the polyol pathway as a mechanism of various organ injuries induced by high concentration of glucose. The polyol pathway consists of two steps. The first is the conversion of glucose to sorbitol, and the second is the conversion of sorbitol to fructose. The key enzyme is aldose reductase that converts glucose to sorbitol. This enzyme is found in many tissues. Hyperglycemia enhances the polyol pathway, resulting in accumulation of sorbitol in the cells. Accumulation of sorbitol in cells causes various organ injuries. High osmotic pressure and high oxidative stress have been proposed as the mechanisms by which the polyol pathway is involved in cell injury. However, the precise mechanism of the polyol pathway is not yet fully understood. It has been observed that high glucose-induced endothelial cell damages may be mediated by activation of the polyol pathway accompanied by augmented oxidative stress. The use of aldose reductase inhibitors suggest that inhibition of the polyol pathway may prevent endothelial cell damages in diabetic conditions.

The beta adrenergic receptor is known to be involved in the process of wound healing, and agonists have shown to delay the wound healing process. It has also been demonstrated that beta-adrenergic receptor-induction inhibits keratinocyte migration, which delays wound healing (Chen et al., J. Invest. Dermatol. 119, 1261-8 (2002)). There are other references for topical applications in the form of aqueous solutions or opthalmic drops of beta-antagonists (Reidy et al., Br. J. Ophthalmol. 78, 377-380 (1994). Denda et al., J. Invest. Dermatol. 121, 142-148 (2003)). Furthermore, the fact that beta blockers are able to increase angiogenesis in infarcted hearts implies that they promote angiogenesis, which may be useful in wound healing (Am J Physiol Heart Circ Physiol. 2005). In addition, propranolol is shown to enhance pulmonary collagen by controlling the ratio of cAMP and cGMP (R C Lindenschmidt and H P Witschi; Pharmacology and Experimental Therapeutics, 232, 346-350 (1985)). However, beta adrenergic receptor blockers have not been reported for their use in diabetic complications like diabetic wound healing, and diabetes wound healing involves a different etiology from regular or traumatic wound healing.

SUMMARY OF INVENTION

The present invention provides methods and compositions for treating diabetic complications arising from diabetes by the administration of beta-adrenergic antagonists or beta-blockers. It further provides methods and compositions for treating chronic diabetic wounds in a diabetic subject comprising topically administering to the subject a therapeutic amount of an agent, such as a beta-adrenergic blocker, which inhibits enhanced aldose reductase activity, increases nitric oxide levels, facilitates fibroblast migration, induces granulation tissue formation and increases vascular perfusion, thereby leading to increased oxygen supply to the healing diabetic wound.

One aspect of the present invention provides a method of treating a diabetic complication in a mammal, comprising administering a therapeutically effective amount of a beta adrenergic blocker, a prodrug thereof, or pharmaceutically acceptable salt thereof to a patient in need of such treatment. The therapeutically effective amount of a beta adrenergic blocker, a prodrug thereof, or pharmaceutically acceptable salt thereof is provided in a pharmaceutically acceptable carrier, vehicle or diluent thereof. Preferably, the diabetic complication is selected from the group consisting of diabetic neuropathy, diabetic nephropathy, diabetic cardiomyopathy, diabetic retinopathy, diabetic cataract, diabetic cystopathy, diabetic corneal keratopathy, diabetic dermopathy, diabetic microangiopathy, myocardial infarction, macular edema, impaired neural conduction and diabetic wounds.

The beta adrenergic blocker, a prodrug thereof, or pharmaceutically acceptable salt thereof may be administered in a sustained release form. The mammal may be a primate, canine, feline, bovine, ovine, porcine, camelid, caprine, rodent or equine. Preferably, the mammal is a human.

The diabetic complication may be treated by administering a therapeutically effective amount of a beta adrenergic blocker, which may include, but is not limited to, acebutolol, alprenolol, amosulalol, arotinolol, atenolol, befunolol, betaxolol, bevantolol, bisoprolol, bopindolol, bretylol, bucumolol, bufetolol, bufuralol, bunitrolol, buprandolol, bupranolol, butofilolol, carazolol, carteolol, carvedilol, celiprolol, cetamolol, cinamolol, cloranolol, dilevatol, entbutolol, epanolol, esmolol, fumolol, indenolol, istalol, labetalol, levobetaxolol, levobunolol, mepindolol, metipranolol, metipropranolol, metoprolol, moprolol, nadolol, nadoxolol, nebivolol, nipradilol, optipranolol, oxprenolol, penbutolol, perbutolol, pindolol, practolol, pronethalol, propranolol, protokylol, sotalol, sulfinalol, talindol, tertatolol, tillisolol, timolol, toliprolol, trasylol, xibenolol and pharmaceutically acceptable salts or solvates thereof. The administration may be conducted hourly, daily, weekly or monthly. The daily administration may involve anywhere from one to six administrations each day.

The beta adrenergic blocker may be administered via an oral, intravenous, intraperitoneal, opthalmic, parenteral, topical, subcutaneous, subdural, intravenous, intramuscular, intrathecal, intraperitoneal, intracerebral, intraarterial, intralesional, localized or pulmonary route. When administered by oral route, the dosage of the beta adrenergic blocker is preferably about 1 mg to 1000 mg. When administered by opthalmic route, the dosage of the beta adrenergic blocker is preferably about 0.001% to 10.0%. When administered by a topical route, the dosage of the beta adrenergic blocker is preferably about 0.001% to 50.0%.

The present invention further provides a pharmaceutical topical composition to treat diabetic wound healing in a patient in need thereof, comprising a therapeutically effective amount of a beta adrenergic blocker, a prodrug thereof, or a pharmaceutically acceptable salt thereof, and a pharmaceutically acceptable topical carrier, vehicle, or diluent, wherein the composition is in the form of a cream, ointment, topical swab, emulsion, spray or lotion.

The present invention also provides a pharmaceutical topical composition to treat diabetic wound healing in a patient in need thereof, comprising a therapeutically effective amount of a beta adrenergic blocker esmolol, a prodrug thereof, or a pharmaceutically acceptable salt thereof, and a pharmaceutically acceptable topical carrier, vehicle, or diluent, wherein the composition is in the form of a cream, gel, topical solution, patch, ointment, topical swab, emulsion, spray or lotion.

The present invention also provides a method of treating diabetic wounds comprising topically administering a therapeutic amount of a beta adrenergic blocker, prodrug thereof, or pharmaceutically acceptable salt there, to a patient in need thereof. Preferably, the beta adrenergic blocker is esmolol. The esmolol used to treat diabetic complications may involve a mechanism selected from the group consisting of inducing nitric oxide production; increasing the level of collagen in the diabetic wound; increasing the vascular perfusion by way of enhanced neo-angiogenesis in the diabetic wound; increasing oxygen supply by way of enhanced vascular perfusion in the diabetic wound; inhibit the increased aldose reductase activity in the diabetic patient; enhancing growth factors such as nerve growth factors, epithelial growth factors, vascular endothelial growth factors, platelet derived growth factors in the diabetic wound, and combinations thereof.

The beta adrenergic blocker may be applied topically in the form of a cream, ointment, topical swab, emulsion, spray or lotion. When the beta adrenergic blocker is esmolol, the esmolol may be applied topically in the form of a cream, gel, topical solution, patch, ointment, topical swab, emulsion, spray or lotion. The mammal may be a primate, canine, feline, bovine, ovine, porcine, camelid, caprine, rodent or equine. Preferably, the mammal is a human.

The present invention further provides a method of treating diabetic complications mediated by aldose reductase in a mammal, comprising administering a therapeutically effective amount of a beta adrenergic blocker having aldose reductase activity, a prodrug thereof, or pharmaceutically acceptable salt thereof to a patient in need thereof. Preferably, the beta adrenergic blocker is esmolol, timolol, or propanolol. The therapeutically effective amount of a beta adrenergic blocker, a prodrug thereof, or pharmaceutically acceptable salt thereof may be provided in a pharmaceutically acceptable carrier, vehicle or diluent thereof.

Preferably, the aldose reductase mediated diabetic complications are selected from the group consisting of diabetic neuropathy, diabetic nephropathy, diabetic cardiomyopathy, diabetic retinopathy, diabetic cataract, diabetic cystopathy, diabetic corneal keratopathy, diabetic dermopathy, diabetic microangiopathy, myocardial infarction, macular edema, impaired neural conduction and diabetic wounds.

DETAILED DESCRIPTION OF INVENTION

In accordance with this detailed description, the following abbreviations and definitions apply. It must be noted that as used herein, the singular forms "a", "and", and "the" include plural referents unless the context clearly dictates otherwise. Thus, for example, reference to "the dosage" includes reference to one or more dosages and equivalents thereof known to those skilled in the art.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

By the term "subject" or "patient" as used herein is meant to include a mammal. The mammal can be a canine, feline, primate, bovine, ovine, porcine, camelid, caprine, rodent, or equine. Preferably the mammal is human.

The term "efficacy" as used herein refers to the effectiveness of a particular treatment regime. Methods of assessing efficacy in treating diabetic complications and wounds would be known to the treating and diagnosing medical professionals.

By the phrases "pharmaceutically acceptable carrier" and "pharmaceutically acceptable excipient" are intended to mean any compound(s) used in forming a part of the formulation that is intended to act merely as a carrier. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The terms "treating", and "treatment", and the like are used herein to generally mean obtaining a desired pharmacological and physiological effect. More specifically, the reagents described herein which are used to treat a subject suffering from a diabetic complication and/or diabetic wound. The diabetic complication may be mediated by aldose reductase, or other mechanism of action such as inhibiting enhance aldose reductase activity, inducing nitric oxide production; increasing the level of collagen in the diabetic wound; increasing the vascular perfusion by way of enhanced neo-angiogenesis in the diabetic wound; increasing oxygen supply by way of enhanced vascular perfusion in the diabetic wound; inhibiting the increased aldose reductase activity in the diabetic patient; enhancing growth factors such as nerve growth factors, epithelial growth factors, vascular endothelial growth factors, platelet derived growth factors in the diabetic wound. The term "treatment", as used herein, covers any treatment of a disease in a mammal, particularly a human.

By "therapeutically effective amount" is meant an amount of an agent, reagent, compound, composition, or combination of such materials disclosed herein that when administered to a mammal is sufficient to be effective against the diabetic complication or diabetic wound.

There are at least 17 million people with diabetes in the United States, and approximately 1 million new cases are diagnosed each year. A majority of the diabetic population is diagnosed with severe diabetic complications, including diabetic neuropathy, diabetic nephropathy, diabetic cardiomyopathy, diabetic retinopathy, diabetic cataract, diabetic cystopathy, diabetic corneal keratopathy, diabetic dermopathy, diabetic microangiopathy, myocardial infarction, macular edema, impaired neural conduction and diabetic wounds. Presently there are limited treatment options for patients suffering from diabetic complications. It is this immediate need for effective treatments for diabetic complications that forms the subject matter of the present invention.

Diabetic wound patients often demonstrate decreased wound inflammation, recurrent wound infections, decreased cutaneous vascular perfusion, poor wound collagen deposition, and scar maturation. Platelet derived growth factor (PDGF) deficiency is associated with the chronic diabetic ulcer and contributes to impaired healing (H D Beer, M T Longaker, S Werner, J Invest Dermatol 109, 132 (1997)). Clinical trials using Regranex® have shown efficacy in improving chronic foot ulcer healing in only half or less of the patients evaluated (D L Steed, J Vasc Surg, 21, 71 (1995)).

An investigation into pathways contributing to impaired diabetic wound healing reveals several factors responsible for poor healing response. Atherosclerosis of major and minor vessels impedes the delivery of oxygen and nutrients to the wound. Neuropathy causes loss of protective sensibility and local trauma. Finally, defective immune defences inhibit cellular phagocytosis of debris and promote infection. Hyperglycemia itself is responsible for the formation of advanced glycation end products (AGE's), which bind cell membranes and extracellular matrix proteins and impede their function. Growth factors such as platelet-derived growth factor, transforming growth factor beta and vascular endothelial growth factor have all been found to be deficient in diabetic wounds, whereas levels of matrix metalloproteinases and superoxide are elevated in diabetic wound fluid.

Chronically elevated blood glucose levels result in reduced leukocyte function and cell malnutrition, which contribute to a high rate of wound infection and associated healing problems in diabetic patients. Diabetic foot ulcers also occur as a result of various other factors. These factors include mechanical changes in conformation of the bony architecture of the foot, peripheral neuropathy, and atherosclerotic peripheral arterial disease, all of which occur with higher frequency and intensity in the diabetic population. Nonenzymatic glycosylation predisposes ligaments to stiffness. Neuropathy causes loss of protective sensation and loss of coordination of muscle groups in the foot and leg, both of which increase mechanical stresses during ambulation. Diabetes is also known to be associated with a variety of alterations in connective tissue metabolism, as a result of which diabetics face the problem of poor wound healing. The loss of collagen related to diabetes may be due to decreased levels of synthesis or enhanced metabolism of newly synthesized collagen or both. These qualitative and quantitative abnormalities contribute to the impaired wound healing observed in diabetic patients.

Among other pathways described above, the polyol pathway has been implicated as a mechanism of various organ injuries (including diabetic foot ulcers) induced by high concentration of glucose. Results of etiologic studies suggest that hyperglycemia induces diabetes-related complications through sorbitol accumulation and protein glycation. The polyol pathway consists of two steps. The first is the conversion of glucose to sorbitol, and the second is the conversion of sorbitol to fructose. The key enzyme is aldose reductase which converts glucose to sorbitol. This enzyme is found in many tissues.

Existing aldose reductase inhibitors include molecules such as tolrestat, zopolrestat, fiderestat, and epalrestat. The present inventions provides the first evidence for the aldose reductase inhibitory activity of certain beta-adrenergic blockers such as esmolol, propranolol, and timolol. The presently discovered aldose reductase inhibitory activity of certain beta-adrenergic blockers positions them as drugs for treatment of aldose reductase mediated diseases, such as diabetic complications. The increased aldose reductase activity results in enhanced accumulation of sorbitol, leading to several diabetic complications. The present invention provides the discovery of aldose reductase inhibitory activity of beta-adrenergic blockers and their use in treatment of diabetic complications, such as diabetic wound healing.

Accumulation of sorbitol in cells causes various organ injuries leading to cutaneous microangiopathy. There are many mechanisms by which diabetes may cause microangiopathy. These include excess sorbitol formation, increased glycation end products, oxidative damage, and protein kinase C over-activity. All of these processes occur in the skin, and the existence of a cutaneous diabetic microangiopathy has been well demonstrated. These microangiopathic changes are associated with abnormalities of skin perfusion. Because the skin plays a thermo regulatory role, there is significant capillary redundancy in normal skin. In diabetic patients, loss of capillaries is associated with a decrease in perfusion reserve. The associated failure of microvascular perfusion to meet the requirements of skin metabolism may result in diverse skin lesions in patients with diabetes, e.g., diabetic wounds.

Neuropathy is another common complication of diabetes, caused by activation of the polyol pathway. Patients with diabetic foot ulceration on the plantar, medial and lateral surfaces of the foot will almost all have clinically significant peripheral neuropathy. The resulting nerve damage manifests as peripheral neuropathy, which predisposes the patient to diabetic ulcer development. The pathology of diabetic neuropathy involves oxidative stress, advanced glycation end products, polyol pathway flux, and protein kinase C activation, which all contribute to the microvascular disease and nerve dysfunction seen in diabetic wounds.

Increases in osmotic pressure and oxidative stress have been proposed as the other mechanisms by which polyol pathway is involved in cell and tissue injury. Accordingly, aldose reductase inhibitors improve cutaneous perfusion, induce nerve regeneration and decrease oxidative stress leading to improved diabetic wound healing.

The methods and compositions of the present invention are designed to detect, treat, and monitor diabetic patients with poor wound healing ability based on measurement of the synthesis of nitric oxide (NO) in specimens taken from the patient under controlled conditions. The invention notes that diabetic patients represent a continuous spectrum of NO synthetic capability, and that diabetics at the lower end of that spectrum have impaired wound healing function.

Recent research on the role of NO in wound inflammation, tissue repair, and microvascular homeostasis reveals that NO is a primary regulator of wound healing (D Bruch-Gerharz, T Ruzicka, V Kolb-Bachofen. J Invest Dermatol. 110, 1 (1998); M R Schaffer et al., Surgery 121, 513 (1997)). A systemic deficiency of endothelial-derived NO has been observed in all diabetics (A Veves et al., Diabetes, 47, 457 (1998); M Huszka et al., Thrombosis Res, 86(2), 173 (1997); S B Williams, J A Cusco, M A Roddy, M T Hohnston, M A Creager, J. Am. Col. Cardiol., 27(3), 567 (1996)), suggesting that NO plays a fundamental role in the pathogenesis of chronic, non-healing lower extremity ulcers (LEU). Consequently, there is a need to correlate NO production with wound healing ability in diabetics. Such a correlation would allow the development of methods to predict the wound healing ability of diabetics based on their production of NO and would provide a useful clinical indicator which could serve as a basis for choosing appropriate therapy.

NO is a small, hydrophobic gaseous free radical, which is an important physiological mediator for autonomic functions such as vasodilation, neurotransmission, and intestinal peristalsis. NO provides cellular signaling by activation of its target molecule, guanylate cyclase, which elevates intracellular concentrations of cyclic guanosine monophosphate (cGMP) (J S Beckman, in Nitric Oxide, J. Lancaster, Jr., Ed. (Academic Press, N.Y.), chap. 1). Cellular signaling is performed without mediation of channels or cellular membrane receptors and is dependent upon the concentration of NO in the cellular environment. NO has a half-life of about five seconds in biological tissues. It is generated by three isoforms of nitric oxide synthase (NOS), which metabolize L-arginine and molecular oxygen to citrulline and NO. Two of the three isoforms are constitutive enzyme systems (cNOS) which are described in neuronal cells (nNOS) and in endothelial cells (eNOS) (D Bruch-Gerharz, T Ruzicka, V Kolb-Bachofen. J Invest Dermatol. 110, 1 (1998)). With these isoforms, increased levels of intracellular calcium activate the enzymes via calmodulin. The calcium-dependent cNOS systems produce low (picomolar) concentrations of NO. The third system is the inducible isoform (iNOS) which is calcium independent. The expression of iNOS is induced by tissue-specific stimuli such as inflammatory cytokines or bacterial lipopolysaccharide (LPS). The inducible isoform releases NO in much higher (nanomolar) concentrations than cNOS, and has potent cytotoxic effects.

The cNOS enzymes are involved in regulating and maintaining skin homeostasis (S Moncada, A Higgs, N Eng J Med 329, 2002 (1993)). The iNOS enzymes appear to be mainly associated with inflammatory and immune responses that are also implicated in certain skin diseases. In human skin keratinocytes, fibroblasts and endothelial cells possess both the cNOS and iNOS isoforms. The wound macrophage and keratinocyte possess the iNOS isoform. In wound healing studies NO synthesis has been shown to occur for prolonged periods (10-14 days) after wounding and macrophages appear to be the major cellular source M R Schaffer, U Tantry, R A van-Wesep, A Barbul. J Surg Res, 71, 25 (1997)). As a mediator of tissue repair, NO has been demonstrated to promote angiogenesis (A Papapetropoulos, G Garcia-Cardena, J A A Madri, W C Sissa. J Clin Invest, 100(12), 3131 (1997)) and cellular migration (Noiri et al., Am. J. Physiol. 279:C794 (1996)), increase wound collagen deposition and collagen cross-linking (M R Schaffer, U Tantry, S S Gross, H L Wasserburg, A Barbul. J Surg Res, 63, 237 (1996)), regulate microvascular homeostasis (vasodilatation) (D Bruch-Gerharz, T Ruzicka, V Kolb-Bachofen. J Invest Dermatol. 110, 1 (1998)), inhibit platelet aggregation (J S Beckman, in Nitric Oxide, J. Lancaster, Jr., Ed. (Academic Press, N.Y.), chap. 1), inhibit the formation of endothelial-leukocyte adhesions (A M Lefer, D J Lefer, Cardiovascular Res. 32, 743 (1996)), modulate endothelial proliferation and apoptosis (Y H Shen, X L Wang, D E Wilcken, FEBS Lett, 433(1-2), 125 (1998)), increase the viability of random cutaneous flaps (S C Um et al., Plast Reconstr Surg. 101 785 (1998); G F Pierce et al., Proc Natl Acad Sci USA. 86, 2229 (1989)), and enhance cellular immunomodulation and bacterial cytotoxicity (J S Beckman, in Nitric Oxide, J. Lancaster, Jr., Ed. (Academic Press, N.Y.), chap. 1).

In diabetics, normal wound repair may be significantly compromised. In general, during the wound healing process, NO provides enhancement of tissue oxygen availability, the inflammatory mediation of repair mechanisms and wound matrix development and remodeling. The major metabolic pathway for NO is to nitrate and nitrite, which are stable metabolites within tissue, plasma, and urine (S Moncada, A Higgs, N Eng J Med 329, 2002 (1993)). Tracer studies in humans have demonstrated that perhaps 50% of the total body nitrate/nitrite originates from the substrate for NO synthesis, L-arginine (P M Rhodes, A M Leone, P L Francis, A D Struthers, S Moncada, Biomed Biophys Res. Commun. 209, 590 (1995); L. Castillo et al., Proc Natl Acad Sci USA 90, 193 (1993). Although nitrate and nitrite are not measures of biologically active NO, plasma and urine samples obtained from subjects after a suitable period of fasting, and optionally after administration of a controlled diet (low nitrate/low arginine), allowing the use of nitrate and nitrite as an index of NO activity (C Baylis, P Vallance, Curr Opin Nephrol Hypertens 7, 59 (1998)).

The invention provides a method of determining whether a diabetic subject is a healing wound diabetic or a non-healing wound diabetic. A "healing wound diabetic" refers to a diabetic subject whose wound healing capability is approximately the same as that of a non-diabetic subject. A "non-healing wound diabetic" refers to a diabetic subject whose wound healing capability is reduced from that of a non-diabetic subject and who consequently is at risk for lower extremity ulcers (LEU). For example, in one clinical study, non-wound healing diabetics were considered to be those patients with a history of one or more diabetic foot ulcers with incomplete healing after 20 weeks of Regranex® treatment. A human or animal with a diabetic condition is a human or animal whose regulation of plasma glucose concentration is defective, usually as a result of insufficient production of insulin or resistance to the physiological effects of insulin. For example, the subject can be a human patient who is diagnosed by a physician as having either type I or type II diabetes.

A subject according to the invention can be any human or animal with a diabetic condition such as diabetes mellitus. The animal may be a mammal. The mammal may be a canine, feline, primate, bovine, ovine, porcine, camelia, caprine, rodent, or equine. Preferably, the subject is a human.

Methods of Administration

One aspect of the invention contemplates the use of beta adrenergic blockers, their prodrugs, or pharmaceutically acceptable salts thereof in the treatment of conditions, including diabetic complications arising from any form of diabetes.

The beta adrenergic blocker may include, but is not limited to, acebutolol, alprenolol, amosulalol, arotinolol, atenolol, befunolol, betaxolol, bevantolol, bisoprolol, bopindolol, bretylol, bucumolol, bufetolol, bufuralol, bunitrolol, buprandolol, bupranolol, butofilolol, carazolol, carteolol, carvedilol, celiprolol, cetamolol, cinamolol, cloranolol,decanoyl, dodecanoyl, dilevatol, entbutolol, epanolol, esmolol, fumolol, indenolol, istalol, labetalol, levobetaxolol, levobunolol, mepindolol, metipranolol, metipropranolol, metoprolol, moprolol, myristoyl, nadolol, nadoxolol, nebivolol, nipradilol, octanoyl, optipranolol, oxprenolol, palmitoyl (U.S. Pat. No. 4,897,417), penbutolol, perbutolol, pindolol, practolol, pronethalol, propranolol, protokylol, sotalol, stanozolol, sulfinalol, talindol, tertatolol, tillisolol, timolol, toliprolol, trasylol, xibenolol, adrenergic blockers, their prodrugs or pharmaceutically acceptable salts thereof. Prodrugs thereof include all derivatives of the beta adrenergic blocker that can deliver the beta adrenergic blocker upon metabolism in the body. For example, all derivatives of esmolol that can deliver esmolol upon metabolism are potential prodrugs of esmolol.

Esmolol has been found to treat diabetic complications such as diabetic wound by various mechanisms, including, but not limited to, inducing nitric oxide production; increasing the level of collagen in the diabetic wound; increasing the vascular perfusion by way of enhanced neo-angiogenesis in the diabetic wound; increasing oxygen supply by way of enhanced vascular perfusion in the diabetic wound; inhibit the increased aldose reductase activity in the diabetic patient; enhancing growth factors such as nerve growth factors, epithelial growth factors, vascular endothelial growth factors, platelet derived growth factors in the diabetic wound, and combinations thereof.

The beta adrenergic blockers of the present invention may have aldose reductase mediating activity. The beta adrenergic blockers having aldose reductase mediating activity may include, but is not limited to, esmolol, timolol, or propanolol. Beta adrenergic blockers having aldose reductase mediating activity are especially useful in the treatment of diabetic complications. For example, esmolol is a preferred beta adrenergic blocker for the treatment of diabetic wound healing. However, all beta adrenergic blockers may be useful in the treatment of any contemplated diabetic complication.

The beta adrenergic blockers, prodrugs and salts thereof intended for wound healing are preferably topically administered in a physiologically acceptable carrier to a subject. However, for treatment of diabetic complications other than diabetic wounds, the beta adrenergic blockers, their prodrugs, or pharmaceutically acceptable salts may also be administered in a variety of ways including but not limited to oral administration, opthalmic administration, parenteral administration, including topical, subcutaneous (s.c.), subdural, intravenous (i.v.), intramuscular (i.m.), intrathecal, intraperitoneal (i.p.), intracerebral, intraarterial, or intralesional routes of administration, localized (e.g., surgical application or surgical suppository), and pulmonary (e.g., aerosols, inhalation, or powder) and as described further below.

The correct dosage of a pharmaceutical composition comprising compounds with the beta adrenergic receptor antagonists will vary according to the pharmaceutical formulation, the mode of application, as well as the particular situs, host and diabetic complication being treated. Other factors including age, body weight, sex, diet, time of administration, rate of excretion, condition of the host, drug combinations, reaction sensitivities and severity of the disease may be readily taken into account by a treating professional or one of skill in the art.

Administration may be carried out continuously or periodically within the maximum tolerated dose. The administration may be conducted, for example, hourly, once every two hours, once every three hours, once every six hours, once every twelve hours, daily, weekly, every two weeks, every three weeks, or monthly, as needed.

The topical route of administration is a preferred route for treatment of diabetic complications such as non-healing diabetic wounds. Suitable compositions for topical administration may include creams, lotions, soaps, shampoos, aerosol, balm, gel, serum, mousse, patch, pump spray, roll-on, topical solution, stick, towelette, footcare product, ointment, wipe, emulsion, cosmetic, topical swab and any combination thereof.

Accordingly, the present invention provides a pharmaceutical composition for topical administration, for the treatment of diabetic wound healing, comprising a beta adrenergic blocker, a prodrug thereof, or a pharmaceutically acceptable salt thereof, and a pharmaceutically acceptable topical carrier, vehicle, or diluent. The topical composition is preferably in the form of a cream, ointment, topical swab, emulsion, spray or lotion. The composition may be provided in sustained release form.

In the treatment of diabetic wound healing, esmolol has been found to be useful. Thus, the present invention provides a pharmaceutical composition for topical administration, for the treatment of diabetic wound healing, comprising esmolol, a prodrug thereof, or a pharmaceutically acceptable salt thereof, and a pharmaceutically acceptable topical carrier, vehicle, or diluent. The topical composition comprising esmolol is preferably in the form of a gel, a patch, topical solution, cream, ointment, topical swab, emulsion, spray or lotion. The composition may be provided in sustained release form.

Depending upon the manner of introduction, the beta adrenergic blockers, their prodrugs, or pharmaceutically acceptable salts may be formulated in various ways. The concentration of therapeutically active ingredient in a formulation for topical administration may vary from a concentration of about 0.001% to 50.0%. Preferably, the concentration of therapeutically active ingredient in a formulation for topical administration may vary from a concentration of about 0.01% to 40.0%. More preferably, concentration of therapeutically active ingredient in a formulation for topical administration may vary from a concentration of about 0.001% to 20.0%.

There are references of existing topical formulations of beta blockers in the forms of opthalmic solutions (drops) and opthalmic gels for treatment of enhanced intraocular pressure (IOP). Transdermal patches of beta-blockers for treatment of cardiac conditions have also been prepared (International Patent Publication No. WO/2000/035439/U.S. Pat. No. 5,362,757). However, there are no existing references to formulation of beta adrenergic blockers for topical application to the skin or dermis. The present invention provides the formulation of beta adrenergic blockers, such as esmolol, as a topical application.

In treating diabetic complications such as diabetic wound, a composition containing esmolol hydrochloride as the active ingredient may be advantageously administered to subject in need by way of a topical preparation, having a concentration of esmolol hydrochloride of about 0.001% to 50.0%.

Preferably, the beta adrenergic blockers, their prodrugs, or pharmaceutically acceptable salts are formulated for topical administration in a suitable inert carrier. For example, the concentration of beta adrenergic blockers, their prodrugs, or pharmaceutically acceptable salts in the carrier solution is typically between about 0.1% to about 50.0%. The dose administered will be determined by route of administration.

The concentration of therapeutically active ingredient in a formulation for oral administration may vary from a concentration of about 1 mg to 1000 mg. The concentration of therapeutically active ingredient in a formulation for opthalmic administration may vary from a concentration of about 0.001% to 10.0%.

For parenteral administration, the beta adrenergic blockers, their prodrugs, or pharmaceutically acceptable salts of the invention can be administered as injectable dosages of a solution or suspension of the substance in a physiologically acceptable diluent with a pharmaceutical carrier, which can be a sterile liquid such as water and oils with or without the addition of a surfactant. Other acceptable diluents include oils of animal, vegetable, or synthetic origin, for example, peanut oil, soybean oil, and mineral oil. In general, glycols such as propylene glycol or polyethylene glycol (PEG) are preferred liquid carriers, particularly for injectable solutions. The beta adrenergic blockers, their prodrugs, or pharmaceutically acceptable salts of this invention can be administered in the form of a depot injection or implant preparation, which can be formulated in such a manner as to permit a controlled or sustained release of the active ingredient(s).

According to one aspect of the invention, a beta adrenergic blocker, their prodrug, or pharmaceutically acceptable salts may be administered alone, or in combination with other agents as discussed above to treat and/or ameliorate a condition such as diabetes complications occurring from any form of diabetes. These reagents can also be used in the preparation of a medicament for use in treating a patient. Administration of therapeutic agents for the treatment of diabetes related conditions can occur prior to, concurrent with, or after administration with the beta adrenergic blockers, their prodrugs, or pharmaceutically acceptable salts. Administration of the subject beta adrenergic blockers, their prodrugs, or pharmaceutically acceptable salts can occur before, during or after any other diabetes treatment modality. Administration of the subject beta adrenergic blockers, their prodrugs, or pharmaceutically acceptable salts can occur hourly, daily, weekly, or monthly as needed, based on the severity of the wound and other factors well known to the skilled medical provider. Preferably, the beta adrenergic blockers, their prodrugs, or pharmaceutically acceptable salts are administered weekly for one or more weeks. The preferred regimen for treatment is continuous or intermittent topical application of the preferred formulation varying as per patient's profile as well as location and severity of diabetic wound.

Pharmaceutical compositions comprising beta adrenergic blockers, their prodrugs, or pharmaceutically acceptable salts may also include pharmaceutically acceptable, non-toxic carriers or diluents, which are vehicles commonly used to formulate pharmaceutical compositions for animal or human administration. The formulations may also contain conventional additives, such as solubilizers, isotonic agents, suspending agents, emulsifying agents, stabilizers and preservatives.

The compositions may be formulated for sustained release. The beta adrenergic blockers, their prodrugs, or pharmaceutically acceptable salts of this invention can be administered in a sustained release form, for example a depot injection, implant preparation, or osmotic pump, which can be formulated in such a manner as to permit a sustained release of the active ingredient. Implants for sustained release formulations are well-known in the art. Implants are formulated as microspheres, slabs, etc. with biodegradable or non-biodegradable polymers. For example, polymers of lactic acid and/or glycolic acid form an erodible polymer that are well-tolerated by the host.

The present invention further provides methods of treating diabetic complications mediated by aldose reductase, comprising administering a therapeutically effective amount of a beta adrenergic blocker, a prodrug thereof, or pharmaceutically acceptable salt thereof having aldose reductase mediating activity. Preferably, the beta adrenergic blocker is esmolol, timolol, or propanolol. The aldose reductase mediated diabetic complications may include, but are not limited to, diabetic neuropathy, diabetic nephropathy, diabetic cardiomyopathy, diabetic retinopathy, diabetic cataract, diabetic cystopathy, diabetic corneal keratopathy, diabetic dermopathy, diabetic microangiopathy, myocardial infarction, macular edema, impaired neural conduction and diabetic wounds.

EXAMPLES

Example 1

Aldose Reductase (AR) Inhibition Studies:

For enzyme inhibition studies, purified human recombinant aldose reductase (expressed in *E. coli*) was used for testing the aldose reductase (AR) inhibitory activity of beta adrenergic antagonists by a spectrophotometric method, using glyceraldehydes as substrate, (Mol. Vis. 2004, 10, 148-154).

Materials:

DL-glyceraldehyde, glucose, lithium sulfate, 2-mercaptoethanol, NADPH, dimethylsulfoxide, TC-199 medium (M-3769), sorbitol, sorbitol dehydrogenase, NAD, and glutathione reductase were purchased from Sigma Chemical Company (St. Louis, Mo.). Beta-adrenergic antagonists including timolol, esmolol, sotalol, nebivolol, carvedilol, metoprolol and labetalol, used in the experiment were obtained as pure active pharmaceutical ingredients (APIs) from local commercial suppliers. The salts of beta antagonists used for the experiments are: timolol maleate, sotalol hydrochloride, labetalol hydrochloride, metoprolol tartrate, nebivolol hydrochloride, esmolol hydrochloride and propranolol hydrochloride.

Rat Lens Aldose Reductase:

Crude aldose reductase (AR) was prepared from rat lens. Eyeballs were removed from 9 week old WNIN male rats obtained from National Center for Laboratory Animal Services, National Institute of Nutrition, Hyderabad, India. Animal care and protocols were in accordance with and approved by Institutional Animal Ethics Committee. Lenses were dissected by posterior approach and homogenized in 10 volumes of 100 mM potassium phosphate buffer pH 6.2. The homogenate was centrifuged at 15,000×g for 30 minutes at 4° C. and the resulting supernatant was used as the source of AR.

Purification of Recombinant Human Aldose Reductase:

Recombinant human aldose reductase was purified from bacterial cultures. Enzyme from expression cultures was extracted and purified essentially as described previously (J Biol Chem 1992; 267: 24833-40) with the exception that affinity chromatography over AffiGel Blue (Bio-Rad) was used as a final purification step.

Aldose Reductase (AR) Assay:

AR activity was assayed according to the method described by Hayman and Kinoshita (J Biol Chem 1965; 240: 877-82). The assay mixture in 1 ml contained 50 µM potassium phosphate buffer pH 6.2, 0.4 mM lithium sulfate, 5 µM 2-mercaptoethanol, 10 µM DL-glyceraldehyde, 0.1 µM NADPH, and enzyme preparation (rat lens or recombinant enzyme). Appropriate blanks were employed for corrections. The assay mixture was incubated at 37° C. and initiated by the addition of NADPH at 37° C. The change in the absorbance at 340 nm due to NADPH oxidation was followed in a Cary Bio 100 spectrophotometer.

Inhibition Studies:

For inhibition studies concentrated stocks of the Beta adrenergic antagonists, timolol, esmolol, sotalol, nebivolol, carvedilol, metoprolol and labetalol were prepared in water. Various concentrations of Beta adrenergic antagonists, as test compounds, were added to the assay mixture and incubated for 5-10 minutes before initiating the reaction by NADPH as described above. The percent of inhibition with test compounds was calculated considering the AR activity in the absence of inhibitor was 100%. The concentration of each test sample giving 50% inhibition ($IC_{50}$) was then estimated.

TABLE 1

Aldose reductase inhibitory IC50 values in µM of beta adrenergic antagonists

| Beta adrenergic receptor antagonist | $IC_{50}$ (µM) |
|---|---|
| Esmolol | 160 |
| Timolol | 250 |
| Propranolol | 350 |
| Sotalol | >350 |
| Nebivolol | >350 |
| Carvedilol | >350 |
| Metoprolol | >350 |
| Labetalol | >350 |

Example 2

Estimation of Sorbitol in Red Blood Cells

The compounds that showed effective aldose reductase inhibition (esmolol, timolol, propranolol) were tested for their potential to inhibit formation of sorbitol in red blood cells (RBC). The cells were incubated with 30 mM glucose in vitro. Sorbitol was estimated by the method of reported by Malone, et al. Diabetes; 1980; 29: 861-864.

TABLE 2

Sorbitol concentration in RBC

| Sr. No. | Condition | Sorbitol (µg/ml) |
|---|---|---|
| 1. | RBC under normal conditions | 12.13 |
| 2. | RBC under 30 mM glucose | 21.83 |
| 3. | RBC under 30 mM glucose + 150 µM of esmolol | 16.16 |
| 4. | RBC under 30 mM glucose + 250 µM of timolol | 17.34 |
| 5. | RBC under 30 mM glucose + 350 µM of propranolol | 18.25 |

Example 3

Animal Experiments: Diabetic Wound Healing

Wistar rats were kept in standard autoclaved rodent cages with ad libitum food (Harland Tekland Irradiated Rodent Diet) and autoclaved water. The rats were housed on Harlan Tek-chip pelleted paper in static micro isolators maintained at 72° F., 60% humidity, and a 12 hour light cycle. The animals were kept at the facility for 10 days to get accustomed to the environment, after the arrival from the vendor. Diabetes was induced in the rats by intraperitoneal injection of 50 mg/kg body weight of streptozocin on 5 consecutive days. The wound was created on the rat by using a contortive scratcher to make a 2 mm incision with 0.57-0.62 mm depth on the dorsal skin of the animal. The area was shaved and sanitized with normal lugol's iodine prior to use of the scratcher.

Compound Administration and Wound Handling:

Esmolol hydrochloride (10%) was administered three times daily or the standard treatment control, by smearing the agent directly onto the wound. The positive control used was platelet derived growth factor that is commercially available. The treatment was continued until the wounds of the treated mice were completely healed.

The wounds were rinsed with normal saline, and the irrigated liquid was collected and centrifuged at 2500 rpm for 5 minutes. The supernatant was discarded and the sediment stained and looked at under a high power microscope for the presence of any abnormal cells. Additionally, the sediment material was diluted in 1 ml of RPMI 450 and the number of macrophages was determined by use of a hemocytometer.

Results of Animal Experiments:

It was observed that the original wound in the vehicle-treated rat did not heal and still had a scab (day 27) after wounding, whereas the wound had completely healed in the skin from the treated animal and wound closure was also observed.

Several wound healing parameters were measured on the day 3, day 7, day 12 and day 19 of the creation of the wound. These parameters are reported in separate tables below. The wound size and weight of the rats was measured every alternate day. Specifically, the length and width of the wound were measured by use of micro vernier calipers, and the tensile strength at the edge of the wound was also recorded every other day. The wound diameter was measured by the same investigator on day 3, 12, 19 by the use of an electronic digital vernier caliper (B&D, Pomanus, N.J.). The caliper was calibrated just before the measurement by adjusting the zero error. The decrease in wound diameter is reported in Table 1.

TABLE 1

Decrease in Wound Diameter

|  | Day 3 | Day 12 | Day 19 | % Decrease |
|---|---|---|---|---|
| Controls (MM) | 1.27 +/− 0.12 | 3.78 +/− 0.24 | 7.89 +/− 0.31 | — |
| Positive Control | 1.16 +/− 0.12 | 1.35 +/− 0.19 | 1.47 +/− 0.34 | 536% |
| Esmolol | 1.28 +/− 0.12 | 1.37 +/− 0.17 | 0.79 +/− 0.28 | 998% |

The contraction of wound was measured by a tension calibrator (Harvard apparatus, Quincy, Mass.) and results are given in Table 2.

TABLE 2

Wound Diameter: Degree of Contraction (%)

|  | Day 3 | Day 12 | Day 19 |
|---|---|---|---|
| Controls | 12.46 +/− 5.8 | 26.78 +/− 11.4 | 58.76 +/− 9.9 |
| Positive Control | 11.98 +/− 6.2 | 37.71 +/− 12.4 | 86.14 +/− 10.2 |
| Esmolol | 12.17 +/− 5.8 | 41.86 +/− 13.2 | 98.64 +/− 9.6 |

The area for evaluation was cut clean by an Eppendorf 10 size scalpel and the tissue was preserved in 10% of phosphate buffered formalin solution. The tissues were removed from this formalin solution and immersed in 100% of ethanol for 6 hours. The tissue were again removed and preserved for evaluation in 10% Bouins solution. The biopsy parameters of wound are reported in Table 3.

TABLE 3

Evaluation of Biopsy Wounds in Diabetic Rats

|  | Day 3 | Day 7 | Day 12 | Day 19 | Total |
|---|---|---|---|---|---|
| Controls | 1.2 +/− 0.4 | 2.3 +/− 0.3 | 2.9 +/− 0.3 | 4.5 +/− 0.4 | 10.9 +/− 1.3 |
| Positive Control | 1.3 +/− 0.2 | 1.5 +/− 0.4 | 1.4 +/− 0.4 | 1.5 +/− 0.5 | 5.9 +/− 1.4 |
| Esmolol | 1.3 +/− 0.3 | 1.3 +/− 0.2 | 1.4 +/− 0.3 | 1.5 +/− 0.3 | 5.5 +/− 1.1 |

Epithelization was measured based on observed new epithelial cells generated on the wound observed under powerful microscope. Scar formation score was measured by the standard digital vernier calipers (B&D, Pomanus, N.J.). The results are reported in Table 4.

TABLE 4

Time Taken for Complete Closure of Wound,
Period of Epithelialization and Scar Formation

|  | Wound Closure (Day) | Period for Epithelization (day) | Scar Formation (Score) |
|---|---|---|---|
| Controls | Not closed | 15.7 +/− 1.8 | 4.9 +/− 0.5 |
| Positive Control | 24.7 +/− 3.4 | 11.8 +/− 2.1 | 2.1 +/− 0.5 |
| Esmolol | 19.6 +/− 2.2 | 9.8 +/− 0.8 | 1.3 +/− 0.4 |

The quantity of exudation from wound was measured by the use of a micropipette (Eppendorf). The results are reported in Table 5.

TABLE 5

Exudation in μl

|  | Day 3 | Day 7 | Day 12 | Day 19 | Total |
|---|---|---|---|---|---|
| Controls | 1.1 +/− 0.3 | 1.8 +/− 0.4 | 2.1 +/− 0.8 | 2.6 +/− 0.7 | 7.6 +/− 1.9 |
| Positive Control | 1.2 +/− 0.3 | 2.3 +/− 0.3 | 3.2 +/− 0.3 | 4.8 +/− 0.2 | 11.5 +/− 0.97 |
| Esmolol | 1.2 +/− 0.2 | 2.7 +/− 0.5 | 3.5 +/− 0.6 | 4.9 +/− 0.2 | 12.3 +/− 1.1 |

Transparency of wound was measured by looking at the refractive index. The results are reported in Table 6.

TABLE 6

Film Transparency

|  | Day 3 | Day 7 | Day 12 | Day 19 | Total |
|---|---|---|---|---|---|
| Controls | 1.8 +/− 0.2 | 2.7 +/− 0.4 | 3.7 +/− 0.3 | 3.8 +/− 0.6 | 11.0 +/− 1.2 |
| Positive Control | 1.7 +/− 0.3 | 3.1 +/− 0.3 | 3.8 +/− 0.4 | 4.1 +/− 0.5 | 12.3 +/− 0.9 |
| Esmolol | 1.7 +/− 0.3 | 2.3 +/− 0.4 | 2.6 +/− 0.6 | 3.3 +/− 0.4 | 9.9 +/− 1.1 |

The wound adherence is reported in Table 7. The adherence is the strength by which the two ends of the wound are attached together and measured by a Velcro index meter.

TABLE 7

Wound Adherence

|  | Day 3 | Day 7 | Day 12 | Day 19 | Total |
|---|---|---|---|---|---|
| Controls | 2.7 +/− 0.3 | 2.3 +/− 0.5 | 2.8 +/− 0.9 | 3.1 +/− 0.8 | 10.9 +/− 1.4 |
| Positive Control | 2.6 +/− 0.4 | 3.2 +/− 0.4 | 3.7 +/− 0.6 | 4.3 +/− 0.6 | 13.8 +/− 1.1 |
| Esmolol | 2.6 +/− 0.4 | 3.3 +/− 0.3 | 3.9 +/− 0.5 | 4.7 +/− 0.5 | 14.5 +/− 0.9 |

Fluid accumulation was measured by volume of fluid obtained from wound using micro pipette as described in Table 8.

TABLE 8

Fluid Accumulation

|  | Day 3 | Day 7 | Day 12 | Day 19 | Total |
|---|---|---|---|---|---|
| Controls | 2.3 +/− 0.3 | 2.8 +/− 0.4 | 3.5 +/− 0.4 | 3.8 +/− 0.5 | 12.4 +/− 0.9 |
| Positive Control | 2.4 +/− 0.3 | 2.8 +/− 0.3 | 3.1 +/− 0.4 | 2.7 +/− 0.6 | 11.0 +/− 0.8 |
| Esmolol | 2.3 +/− 0.4 | 2.7 +/− 0.5 | 2.6 +/− 0.7 | 2.5 +/− 0.5 | 10.1 +/− 1.2 |

The ease of removal of the wound was measured by a Velcro index meter and reported in Table 9.

TABLE 9

| | Ease of Removal from Wounds | | | | |
|---|---|---|---|---|---|
| | Day 3 | Day 7 | Day 12 | Day 19 | Total |
| Controls | 2.7 +/− 0.2 | 2.9 +/− 0.1 | 3.1 +/− 0.5 | 3.6 +/− 0.5 | 12.3 +/− 0.5 |
| Positive Control | 2.6 +/− 0.4 | 2.8 +/− 0.3 | 2.8 +/− 0.4 | 2.5 +/− 0.3 | 10.7 +/− 1.1 |
| Esmolol | 2.6 +/− 0.2 | 2.8 +/− 0.3 | 2.7 +/− 0.5 | 2.5 +/− 0.4 | 10.6 +/− 1.4 |

Flexibility of wound was measured by the placidness observed by the normal skin of the same animal compared to the wound area and reported in Table 10.

TABLE 10

| | Flexibility | | | | |
|---|---|---|---|---|---|
| | Day 3 | Day 7 | Day 12 | Day 19 | Total |
| Controls | 2.1 +/− 0.5 | 2.7 +/− 0.4 | 2.3 +/− 0.8 | 1.9 +/− 0.9 | 7.0 +/− 0.9 |
| Positive Control | 2.2 +/− 0.6 | 2.4 +/− 0.7 | 3.7 +/− 1.1 | 4.0 +/− 0.7 | 12.3 +/− 3.2 |
| Esmolol | 2.3 +/− 0.2 | 2.4 +/− 0.5 | 3.5 +/− 0.6 | 3.9 +/− 0.8 | 12.1 +/− 2.9 |

Example 4

Measurement of Nitric Oxide

Fresh tissue (approximately 0.2 g) was added to 1 ml cold homogenizing buffer (20 mmol/l HEPES-KOH, pH 7.9; 25% glycerol; 420 mmol/l NaCl; 1.5 mmol/l MgCl2; 0.2 mmol/l EDTA; 0.5 mmol/l dithiothreitol; 0.2 mmol/l phenylmethylsulphonyl fluoride). The buffered tissues were homogenized at maximum speed for 5 seconds and cooled in ice-water for 30 seconds. This procedure was repeated five times to ensure complete tissue destruction.

Deprotinization:

Two volumes of 100% cold ethanol were added to the homogenized samples; these were vortexed and incubated on ice for 30 minutes. The homogenate was centrifuged at 12,000×g for 5 minutes at 4° C., and the supernatant transferred to a new tube on ice for NO measurement.

Measurement of Nitrite/Nitrate:

A rapid-response chemiluminescence analyzer was used to measure total gas phase NO (nitrate/nitrite). NO gas reacts with ozone, producing energy in the form of light, and the light is proportional to the quantity of NO present. The emission was measured using a luminometer to determine NO concentration.

The sample tube was securely connected to a Zero Gas Filter (Sievers Instruments) and room air passed through the device for 5 minutes. The linearity of analyser response was interpolated using four repeat calibrations (blank, 1, 10, 50, 100 and 200 mmol/l respectively; a lower limit of <1 nmol/l was demonstrated for the present instrument). The samples (10 ml) were injected into a helium-purged vessel containing 0.8% vanadium chloride in hydrochloric acid to liberate gaseous NO from the dissolved NO and nitrite. The sample gas was then exposed to the ozone in the reaction vessel to form activated nitrogen dioxide ($NO_2$), which was detected using a red-sensitive photomultiplier tube, and the output recorded using an integrating pen recorder. For each sample, the area under the curve was converted to NO concentration.

TABLE 11

| | NO increase | | | | | |
|---|---|---|---|---|---|---|
| | Day 3 | Day 7 | Day 12 | Day 19 | Total | % Increase |
| Controls | 1256 | 1243 | 1745 | 1781 | 6025 | |
| Positive Control | 1179 | 2317 | 2431 | 1927 | 7854 | 30% |
| Esmolol | 1219 | 2657 | 3231 | 2115 | 9222 | 53% |

Example 5

Measurement of Collagen

The synthesis of the 19 known collagens occurs within the cell, as it does for other proteins. The collagen molecule is characterized by the repeating sequence Gly-X-Y, with X often being proline and Y often being hydroxyproline. Hydroxyproline is the end product of collagen breakdown. For this reason, tissue hydroxyproline level is an indirect and objective variable of tissue collagen production. In many experimental studies, hydroxyproline has been used to assess tissue collagen production.

Collagen levels in the tissue were measured by use of high performance liquid chromatography (HPLC) for separating and quantitating the levels of hydroxyproline from the rat tissue. A reverse-phase Nova-Pak $C_{18}$ column and solvent system (140 mM sodium acetate, 0.05% triethylamine (TEA), 6% acetonitrile) were used, resulting in complete separation of hydroxyproline. Recovery of standards ranged from 89 to 103% and intra-assay variability was <8%. Additionally, [$^3$H]hydroxyproline measurements were used to examine changes in collagen turnover in the rat labeled with [$^3$H]proline and "chased" in the presence of 10 mM unlabeled proline.

TABLE 12

| | Day 3 | Day 7 | Day 12 | Day 19 | Total | % Increase |
|---|---|---|---|---|---|---|
| Controls | 139 | 142 | 156 | 173 | 610 | |
| Positive Control | 127 | 259 | 243 | 276 | 905 | 48% |
| Esmolol | 124 | 287 | 325 | 288 | 1024 | 68% |

Although the present invention has been described in detail with reference to examples below, it is understood that various modifications can be made without departing from the spirit of the invention, and would be readily known to the skilled artisan.

We claim:

1. A pharmaceutical composition, comprising a therapeutically effective diabetic wound treating amount of a beta adrenergic blocker having aldose reductase inhibitory activity selected from the group consisting of acebutolol, atenolol, betaxolol, bevantolol, bisoprolol, celiprolol, cetamolol, epanolol, esmolol, levobetaxolol, practolol, and pharmaceutically acceptable salts thereof, and a pharmaceutically acceptable topical carrier, vehicle, or diluent, wherein the composition is a locally acting topical dermal composition.

2. The composition of claim 1, wherein the beta adrenergic blocker is esmolol.

3. A method of treating a diabetic wound mediated by aldose reductase in a mammal, comprising administering the composition of claim 1 to a patient in need thereof.

4. The method of claim 3, wherein the beta adrenergic blocker is esmolol.

5. The composition of claim 1, wherein the composition is in the form of a cream, lotion, soap, shampoo, aerosol, balm, gel, serum, mousse, patch, spray, roll-on, topical solution, stick, towelette, ointment, wipe, emulsion, cosmetic, or topical swab.

6. The composition of claim 5, wherein the composition is in the form of a cream, gel, topical solution, patch, ointment, topical swab, emulsion, spray or lotion.

7. The composition of claim 1, wherein the composition is in a sustained release form.

8. The composition of claim 1, wherein the beta adrenergic blocker having aldose reductase inhibitory activity is esmolol hydrochloride.

9. The composition of claim 1, wherein the composition is in the form of a gel.

10. The method of claim 3, wherein the beta adrenergic blocker is esmolol hydrochloride.

* * * * *

UNITED STATES PATENT AND TRADEMARK OFFICE
CERTIFICATE OF CORRECTION

PATENT NO. : 8,686,051 B2
APPLICATION NO. : 12/524823
DATED : April 1, 2014
INVENTOR(S) : Deshpande et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this
Thirtieth Day of May, 2017

Michelle K. Lee
*Director of the United States Patent and Trademark Office*